United States Patent
Tran et al.

(10) Patent No.: US 6,333,329 B2
(45) Date of Patent: *Dec. 25, 2001

(54) 6-(4-ARYLALKYLPIPERAZIN-1-YL) BENZODIOXANE AND 6-(ARYLALKYLPIPERAZIN-1-YL) CHROMANE DERIVATIVES: DOPAMINE RECEPTOR SUBTYPE SPECIFIC LIGANDS

(75) Inventors: Jennifer N. Tran, Guilford; Andrew Thurkauf, Danbury, both of CT (US)

(73) Assignee: Neurogen Corporation, Branford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/761,048

(22) Filed: Jan. 16, 2001

Related U.S. Application Data

(63) Continuation of application No. 09/343,309, filed on Jun. 30, 1999, now Pat. No. 6,177,566.
(60) Provisional application No. 60/091,250, filed on Jun. 30, 1998.

(51) Int. Cl.$^7$ .................................................. A61K 31/496
(52) U.S. Cl. .................. 514/254.11; 544/376; 544/377
(58) Field of Search .................................. 544/376, 377; 514/254.11

(56) References Cited

U.S. PATENT DOCUMENTS

| | | | | |
|---|---|---|---|---|
| 5,424,313 | * | 6/1995 | Hartog et al. | 514/254 |
| 5,753,662 | * | 5/1998 | Peglion et al. | 514/254 |
| 5,859,246 | * | 1/1999 | Thurkauf et al. | 544/392 |
| 6,177,566 | * | 1/2001 | Tran et al. | 544/376 |

FOREIGN PATENT DOCUMENTS

9833784 * 8/1998 (WO).

OTHER PUBLICATIONS van Steen et al, *J. Med. Chem.* 37 p. 2761–2773, (1994).*

* cited by examiner

*Primary Examiner*—Emily Bernhardt
(74) *Attorney, Agent, or Firm*—McDonnell Boehnen Hulbert & Berghoff; Steven J. Sarussi

(57) ABSTRACT

Disclosed are compounds of the formula:

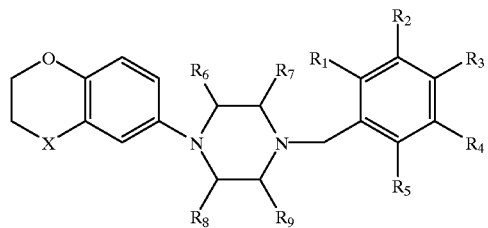

or the pharmaceutically acceptable acid addition salts thereof wherein:

$R_1$, $R_2$, $R_3$, $R_4$ and $R_5$ are the same or different and represent hydrogen, halogen, $C_1$–$C_6$ alkyl, $C_1$–$C_6$ alkoxy, $C_1$–$C_4$ alkylthio, hydroxy, amino, mono- or di($C_1$–$C_6$)alkylamino, cyano, nitro, trifluoromethyl or trifluoromethoxy; and X is oxygen, a bond, $C_1$–$C_2$ alkylene, or methyleneoxy, which compounds are useful for the treatment and/or prevention of neuropsychological disorders including, but not limited to, schizophrenia, mania, dementia, depression, anxiety, compulsive behavior, substance abuse, Parkinson-like motor disorders and motion disorders related to the use of neuroleptic agents.

29 Claims, No Drawings

6-(4-ARYLALKYLPIPERAZIN-1-YL) BENZODIOXANE AND 6-(ARYLALKYLPIPERAZIN-1-YL) CHROMANE DERIVATIVES: DOPAMINE RECEPTOR SUBTYPE SPECIFIC LIGANDS

This application is a continuation of application Ser. No. 09/343,309, filed Jun. 30, 1999, now U.S. Pat. No. 6,177,566, which claims the benefit of U.S. Provisional application Serial No. 60/091,250, filed Jun. 30, 1998.

BACKGROUND OF THE INVENTION

1. Field of the Invention

This invention relates to 6-(4-arylalkylpiperazin-1-yl)benzodioxanes and 6-(4-arylalkylpiperazin-1-yl)chromanes and pharmaceutical compositions containing such compounds. It also relates to the use of such compounds in the treatment or prevention of psychotic disorders such as schizophrenia and other central nervous system diseases.

2. Description of the Related Art

The therapeutic effect of conventional antipsychotics, known as neuroleptics, is generally believed to be exerted through blockade of dopamine receptors. However, neuroleptics are frequently responsible for undesirable extrapyramidal side effects (EPS) and tardive dyskinesias, which are attributed to blockade of $D_2$ receptors in the striatal region of the brain. The dopamine $D_4$ receptor subtype has recently been identified (Nature, 350: 610 (Van Tol et al., 1991); Nature, 347: 146 (Sokoloff et al., 1990)). Its unique localization in limbic brain areas and its differential recognition of various antipsychotics indicates that the $D_4$ receptor plays a major role in the etiology of schizophrenia. Selective $D_4$ antagonists are considered effective antipsychotics free from the neurological side effects displayed by conventional neuroleptics.

SUMMARY OF THE INVENTION

This invention provides novel compounds of Formula I which interact with dopamine subtypes. Accordingly, a broad embodiment of the invention is directed to a compound of Formula I:

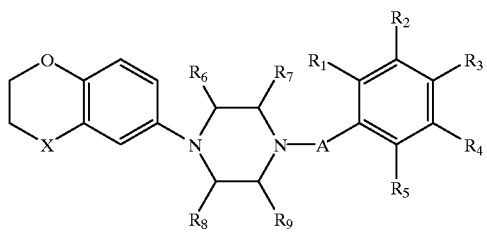

or pharmaceutically acceptable addition salts thereof wherein:

A is $C_1$–$C_4$ alkylene optionally substituted with $C_1$–$C_2$ alkyl;

$R_1$, $R_2$, $R_3$, $R_4$ and $R_5$ independently represent hydrogen, halogen, $C_1$–$C_6$ alkyl, $C_1$–$C_6$ alkoxy, $C_1$–$C_6$ alkylthio, hydroxy, amino, mono- or di($C_1$–$C_6$)alkylamino, cyano, nitro, perfluoroalkyl or perfluoroalkoxy; and $R_6$, $R_7$, $R_8$, and $R_9$ independently represent hydrogen or $C_1$–$C_6$ alkyl; and X is oxygen, a bond, $C_1$–$C_2$ alkylene, or methyleneoxy.

Dopamine $D_4$ receptors are concentrated in the limbic system (Science, 265: 1034 (Taubes, 1994)) which controls cognition and emotion. Therefore, compounds that interact with these receptors are useful in the treatment of cognitive disorders. Such disorders include cognitive deficits which are a significant component of the negative symptoms (social withdrawal and unresponsiveness) of schizophrenia. Other disorders include those involving memory impairment or attention deficit disorders.

Compounds of the present invention demonstrate high affinity and selectivity in binding to the $D_4$ receptor subtype. These compounds are therefore useful in treatment of a variety of neuropsychological disorders, such as, for example, schizophrenia, psychotic depression and mania. Other dopamine-mediated diseases such as Parkinsonism and tardive dyskinesias can also be treated directly or indirectly by modulation of $D_4$ receptors.

Compounds of this invention are also useful in the treatment of depression, memory-impairment or Alzheimer's disease by modulation of $D_4$ receptors since they exist selectively in areas known to control emotion and cognitive functions.

Thus, in another aspect, the invention provides methods for treatment and/or prevention of neuropsychochological or affective disorders including, for example, schizophrenia, mania, dementia, depression, anxiety, compulsive behavior, substance abuse, memory impairment, cognitive deficits, Parkinson-like motor disorders, e.g., Parkinsonism and dystonia, and motion disorders related to the use of neuroleptic agents. In addition, the compounds of the invention are useful in treatment of depression, memory-impairment or Alzheimer's disease. Further, the compounds of the present invention are useful for the treatment of other disorders that respond to dopaminergic blockade, e.g., substance abuse and obsessive compulsive disorder. These compounds are also useful in treating the extrapyramidal side effects associated with the use of conventional neuroleptic agents.

In yet another aspect, the invention provides pharmaceutical compositions comprising compounds of Formula I.

In another aspect, the invention provides intermediates useful in the preparation of compounds of Formula I.

DETAILED DESCRIPTION OF THE INVENTION

As mentioned above, the invention encompasses 6-(4-Arylalkylpiperazin-1-yl)benzodioxane and 6-(4-Arylalkylpiperazin-1-yl)chromane derivatives of Formula I. Preferred compounds of Formula I are those where X is oxygen or methylene. Still other preferred compounds of Formula I are those where $R_1$, $R_2$, and $R_5$ are hydrogen and $R_3$ and $R_4$ are independently hydrogen, halogen, $C_1$–$C_6$ alkyl, or $C_1$–$C_6$ alkoxy. Other preferred compounds of Formula I are those where $R_6$, $R_7$, $R_8$, and $R_9$ are independently hydrogen, methyl, or ethyl.

Other preferred compounds of Formula I are those where A is methylene or ethylene, each of which is optionally substituted independently with a $C_1$–$C_2$ group. More preferably, A is methylene.

Preferred compounds of the invention include those of Formula IA:

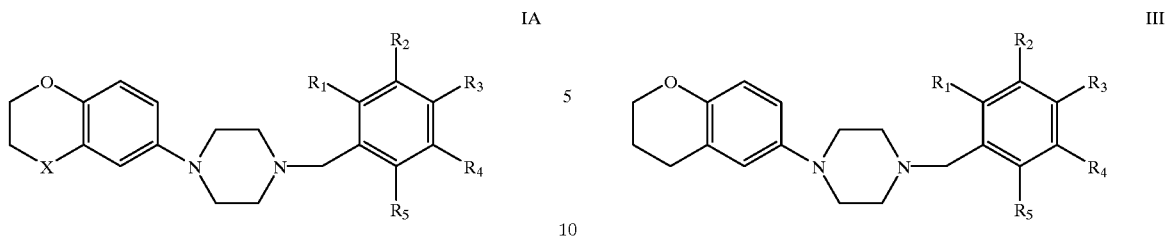

wherein:

R$_1$, R$_2$, R$_3$, R$_4$ and R$_5$ independently represent hydrogen, halogen, C$_1$–C$_6$ alkyl, C$_1$–C$_6$ alkoxy, C$_1$–C$_4$ alkylthio, hydroxy, amino, mono- or di(C$_1$–C$_6$)alkylamino, cyano, nitro, trifluoromethyl or trifluoromethoxy; and X is oxygen, a bond, methyleneoxy, or C$_1$–C$_2$ alkylene.

Preferred compounds of Formula IA are those where R$_1$, R$_2$, R$_3$, R$_4$, and R$_5$ independently represent hydrogen, halogen, C$_1$–C$_6$ alkyl, or C$_1$–C$_6$ alkoxy.

Other preferred compounds of Formula IA are those where R$_1$, R$_2$, and R$_5$ are hydrogen.

More preferred compounds of Formula IA are those where R$_1$, R$_2$, and R$_5$ are hydrogen and R$_3$ and R$_4$ independently represent hydrogen, halogen, C$_1$–C$_6$ alkyl, or C$_1$–C$_4$ alkoxy, where not both R$_3$ and R$_4$ are hydrogen.

Particularly preferred compounds of Formula IA are those where R$_3$ and R$_4$ independently represent hydrogen, fluoro, chloro, bromo, methyl, ethyl, methoxy, or ethoxy, where not both R$_3$ and R$_4$ are hydrogen.

Other particularly preferred compounds of Formula IA are those where X is a bond or methyleneoxy and R$_3$ and R$_4$ independently represent hydrogen, fluoro, chloro, bromo, methyl, ethyl, methoxy, or ethoxy.

The present invention further encompasses compounds of Formula II:

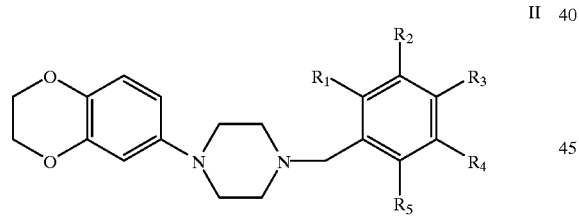

wherein R$_1$, R$_2$, R$_3$, R$_4$ and R$_5$ are defined as above for Formula I.

Preferred compounds of Formula II are those where R$_1$, R$_2$, R$_3$, R$_4$, and R$_5$ independently represent hydrogen, halogen, C$_1$–C$_6$ alkyl, or C$_1$–C$_6$ alkoxy.

Other preferred compounds of Formula II are those where R$_1$, R$_2$, and R$_5$ are hydrogen.

More preferred compounds of Formula II are those where R$_1$, R$_2$, and R$_5$ are hydrogen and R$_3$ and R$_4$ independently represent hydrogen, halogen, C$_1$–C$_6$ alkyl, or C$_1$–C$_4$ alkoxy, where not both R$_3$ and R$_4$ are hydrogen.

Particularly preferred compounds of Formula II are those where R$_3$ and R$_4$ independently represent hydrogen, fluoro, chloro, bromo, methyl, ethyl, methoxy, or ethoxy, where not both R$_3$ and R$_4$ are hydrogen.

The present invention further encompasses compounds of Formula III:

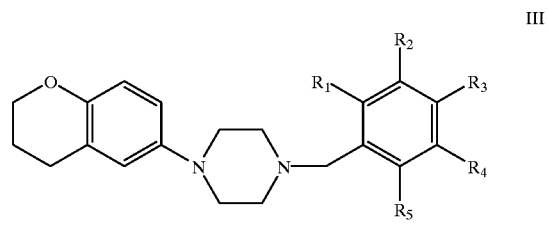

wherein R$_1$, R$_2$, R$_3$, R$_4$ and R$_5$ are defined as above for Formula I.

Preferred compounds of Formula III are those where R$_1$; R$_2$, R$_3$, R$_4$, and R$_5$ independently represent hydrogen, halogen, C$_1$–C$_6$ alkyl, or C$_1$–C$_6$ alkoxy.

Other preferred compounds of Formula III are those where R$_1$, R$_2$, and R$_5$ are hydrogen.

More preferred compounds of Formula III are those where R$_1$, R$_2$, and R$_5$ are hydrogen and R$_3$ and R$_4$ independently represent hydrogen, halogen, C$_1$–C$_6$ alkyl, or C$_1$–C$_4$ alkoxy, where not both R$_3$ and R$_4$ are hydrogen.

Particularly preferred compounds of Formula III are those where R$_3$ and R$_4$ independently represent hydrogen, fluoro, chloro, bromo, methyl, ethyl, methoxy, or ethoxy, where not both R$_3$ and R$_4$ are hydrogen.

The invention also provides intermediates useful in preparing compounds of Formula I. These intermediates have Formulae IV-A, IV-B, IV-C, IV-D, IV-E, and IV-F.

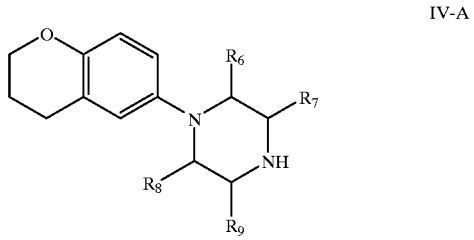

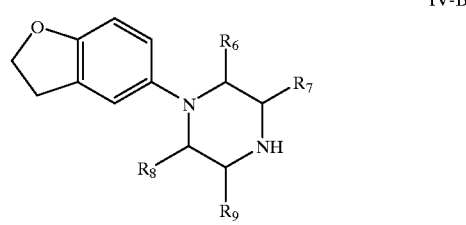

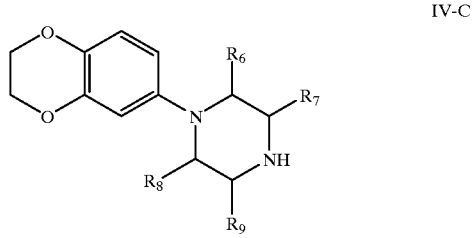

-continued

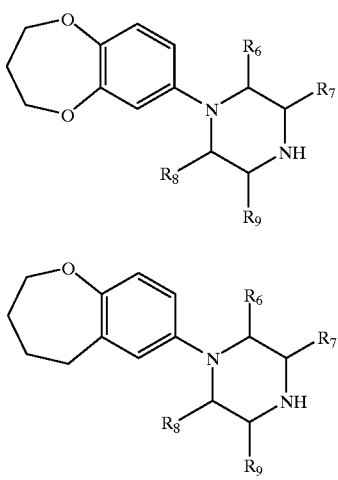

IV-D

IV-E

In each of Formulae IV-A-F, $R_6$, $R_7$, $R_8$, and $R_9$ independently represent hydrogen or $C_1$–$C_6$ alkyl. Particularly preferred compounds of Formulae IV-A-F, are those where $R_6$, $R_7$, $R_8$, and $R_9$ are all hydrogen.

In certain situations, the compounds of Formula I may contain one or more asymmetric carbon atoms, so that the compounds can exist in different stereoisomeric forms. These compounds can be, for example, racemates or optically active forms. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral HPLC column.

Representative compounds of the present invention, which are encompassed by Formula I, include, but are not limited to the compounds in Table 1 and their pharmaceutically acceptable acid addition salts. In addition, if the compound of the invention is obtained as an acid addition salt, the free base can be obtained by basifying a solution of the acid salt. Conversely, if. the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds.

Non-toxic pharmaceutical salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—$(CH_2)_n$—COOH where n is 0–4, and the like. Those skilled in the art will recognize a wide variety of non-toxic pharmaceutically acceptable addition salts.

The present invention also encompasses the acylated prodrugs of the compounds of Formula I. Those skilled in the art will recognize various synthetic methodologies which may be employed to prepare non-toxic pharmaceutically acceptable addition salts and acylated prodrugs of the compounds encompassed by Formula I.

Where a compound exists in various tautomeric forms, the invention is not limited to any one of the specific tautomers. The invention includes all tautomeric forms of a compound.

By "$C_1$–$C_6$ alkyl" or "lower alkyl" in the present invention is meant straight or branched chain alkyl groups having 1–6 carbon atoms, such as, for example, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. Preferred $C_1$–$C_6$ alkyl groups are methyl, ethyl, propyl, butyl, cyclopropyl and cyclopropylmethyl.

By "$C_1$–$C_6$ alkoxy" or "lower alkoxy" in the present invention is meant straight or branched chain alkoxy groups having 1–6 carbon atoms, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy.

By the term "halogen" in the present invention is meant fluorine, bromine, chlorine, and iodine.

Representative 6-(4-arylalkylpiperazin-1-yl) benzodioxane and 6-(4-arylalkylpiperazin-1-yl)chromanes of the present invention are shown in Table 1.

TABLE 1

| Compound 1 |
|---|
| 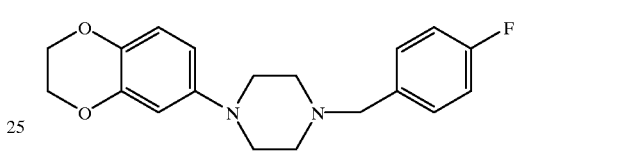 |
| Compound 2 |
| 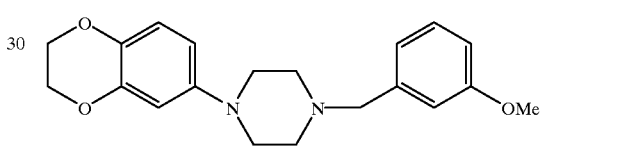 |
| Compound 3 |
| 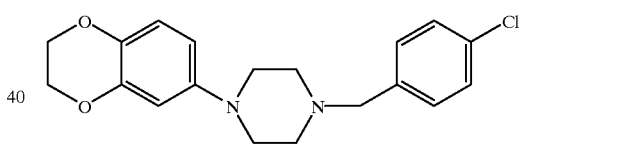 |
| Compound 4 |
| 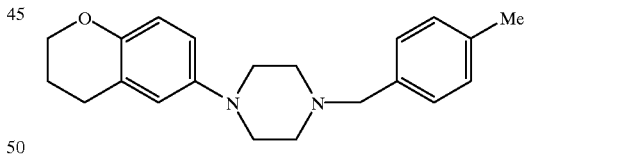 |

The invention also pertains to the use of compounds of general Formula I in the treatment of neuropsychological disorders. The interaction of compounds of the invention with dopamine receptors is shown in the examples. This interaction results in the pharmacological activity of these compounds.

The compounds of general formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general formula I and a pharmaceutically acceptable carrier. One or more compounds of general formula I may be present in association with one or more non-toxic pharmaceutically acceptable carriers and/or diluents and/or adjuvants and if desired other active ingredients. The pharmaceutical compositions containing compounds of general formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starcha, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

A representative synthesis of the 6-(4-arylalkylpiperazin-1-yl)benzodioxanes and 6-(4-arylalkylpiperazin-1-yl)chromanes of the invention is presented in Scheme I. Those having skill in the art will recognize that the starting materials may be varied and additional steps employed to produce compounds encompassed by the present invention.

Scheme I

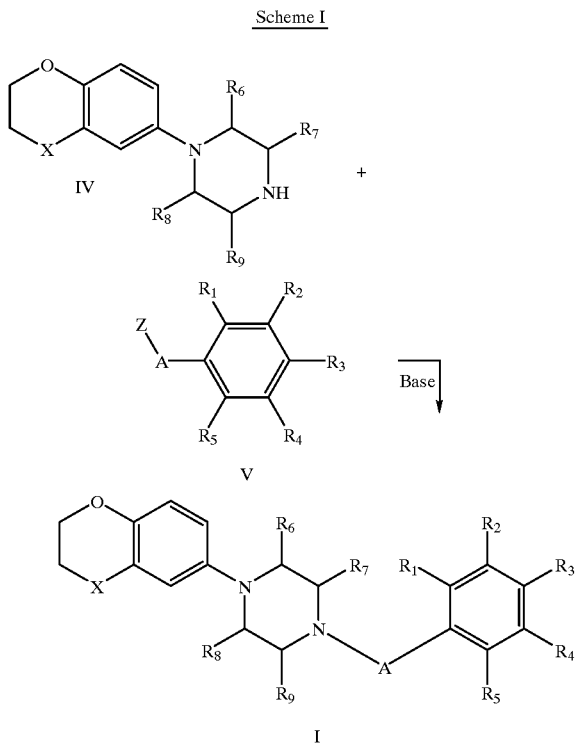

In Scheme I, A, $R_1$–$R_9$ and X are as defined above for Formula I, and Z is a leaving group.

Thus, for example, a 5-piperazinyl-2,3-dihydrobenzo[b]furan (IV, X is a bond), a 1-(1,4-benzodioxan-6-yl)piperazine (IV, X=oxygen), a 1-(chroman-6-yl)piperazine (IV, X=—CH$_2$—), or a 7-piperazinyl-2H,3H,4H,5H-benzo[f]oxepin (IV, X is —CH$_2$CH$_2$—) may be reacted with an appropriately substituted alkylating agent (V), e.g., a benzylic alkylating agent, in the presence of a suitable base to afford a compound of Formula I.

The leaving group (Z) on alkylating agent V may be a halide, sulphonate ester or the like. Where they are not commercially available, the compounds of general structure V may be prepared by procedures analogous to those described in literature. The compounds of general structure V are either known or capable of being prepared by the methods known in the art. Those having skill in the art will recognize that the starting material may be varied and additional steps employed to produce compounds encompassed by the present invention. The base employed may be an inorganic base such as potassium carbonate, sodium hydroxide or the like; or an organic base such as triethylamine, pyridine or the like.

The disclosures of all articles and references mentioned in this application, including patents, are incorporated herein by reference.

The preparation of the compounds of the present invention is illustrated further by the following examples which are not to be construed as limiting the invention in scope or spirit to tne specific procedures and compounds described in them.

EXAMPLE 1

1-(1,4-Benzodioxan-6-yl)piperazine

A solution of 1,4-benzodioxan-6-amine (2.00 g, 13.2 mmol), bis-(2-choroethyl)amine hydrochloride (3.54 g, 19.8 mmol), and potassium carbonate (1.83 g, 13.2 mmol) in of 20 mL chlorobenzene is heated to reflux for 24 hours. The dark brown reaction mixture is then partitioned between 3N NaOH and methylene chloride. The organic layer is separated, dried over Mg$_2$SO$_4$, filtered and concentrated. Purification by flash column chromatography (8% methanol/methylene chloride on silica) provides 0.88 g (30%) of the desired 1-(1,4-benzodioxan-6-yl)piperazine as a white solid (m.p. 138° C., TLC $R_f$ 0.37 with 10% methanol/methylene chloride).

EXAMPLE 2

1-(Chroman-6-yl)piperazine

1. A solution of 4-chromanone (2.00 g, 13.50 mmol) in 20 mL acetic acid is added to a suspension of of zinc dust (20 g) in acetic acid (40 mL). The mixture is heated at 100° C. for 16 h. After cooling to room temperature, the excess zinc is filtered off and the solvent is evaporated. The residue was stirred is water (20 mL), basified with NaOH pellets and extracted with ethyl acetate (20 mL). The organic layer is dried over Mg$_2$SO$_4$, filtered and concentrated. Purification by flash column chromatography (10% ethyl acetate-hexane) affords 1.63 g (91%) of 4-chroman as a yellow oil, TLC $R_f$ 0.50 (10% ethyl acetate:hexane).

2. 4-chroman (1.63 g, 12.16 mmol) from part 1 of this example is treated with 70% HNO$_3$ (6 mL) at 15–20° C. The mixture is stirred at room temperature for 1 hr. The solution is cooled 0° C. with ice water, extracted with ethyl acetate, and concentrated. This crude material is then dissolved in ethanol (50 mL), treated with Raney Nickel (1 g) and hydrogenated for 3 h at room temperature. The resulting mixture is filtered, concentrated, and purified by flash column chromatography (20% ethyl acetate-hexane) to afford 0.48 g (26%) of 6-aminochroman as a yellow oil. TLC $R_f$ 0.28 (35% ethyl acetate:hexane).

3. A solution of 6-aminochroman from part 2 of this example (0.300 g, 2.013 mmol), bis-(2-choroethyl)amine hydrochloride (0.539 g, 3.020 mmol) and potassium carbonate (0.278 g, 2.013 mmol) in 10 mL chlorobenzene is heated at reflux for 24 h . The dark brown reaction mixture is then partitioned between 3N NaOH and methylene chloride. The organic layer is separated, dried over Mg$_2$SO$_4$, filtered and concentrated. Purification by flash column chromatography (5% methanol-methylene chloride) affords 0.157 g (36%) of 1-(chroman-6-yl)piperazine as a white solid, TLC $R_f$ 0.35 (elution with 10% hanol-methylene chloride).

EXAMPLE 3

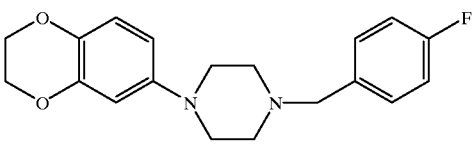

1-(1,4-Benzodioxan-6-yl)-4-(4-fluorobenzyl)piperazine Oxalate

A solution of 1-(1,4-benzodioxan-6-yl)piperazine prepared as described in Example 1 (0.146 g, 0.663 mmol) in CH₃CN (5 mL) is treated with potassium carbonate (0.458 g, 3.32 mmol) and 4-fluorobenzyl chloride (0.144 g, 0.995 mmol). The mixture is heated at ref lux for 4 hours. The resulting mixture is then cooled to room temperature and washed successively with saturated aqueous NH₄Cl (20 mL) and saturated aqueous NaCl (20 mL). The organic portion is dried over Mg₂SO₄, filtered and concentrated. Purification by flash column chromatography (30% ethyl acetate-hexane) gives 0.074 g (34%) of 1-(1,4 benzodioxan-6-yl)-4-(4-fluorobenzyl)piperazine as a white solid (TLC $R_f$ 0.35; 30% ethyl acetate:hexane). A solution of this material in 1 mL of ethanol is treated with oxalic acid (0.020 g, 0.225 mmol) and concentrated to give 1-(1-(1,4-benzodioxan-6-yl)-4-(4-fluorobenzyl)piperazine oxalic acid salt (Compound 1) 0.079 g (88%), m.p. 177–179° C.

EXAMPLE 4

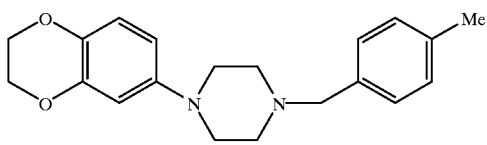

1-(Chroman-6-yl)-4-(4-methylbenzyl)piperazine Oxalate

A solution of 1-(chroman-6-yl)piperazine prepared as described in Example 2 (0.157 g, 0.723 mmol) in CH3CN (5 mL) is treated with potassium carbonate (0.500 g, 3.615 mmol) and 4-methylbenzyl chloride (0.102 g, 0.723 mmol). The mixture is heated at reflux for 4 hours, cooled to room temperature and diluted with CH₂Cl₂ (20 mL). This mixture is washed successively with saturated aqueous NH₄Cl (20 mL) and saturated aqueous soduium chloride (20 mL). The organic phase is dried over MgSO₄ and concentrated. Purification by flash chromatography (30% ethyl acetate-hexane) gives 40 mg (17%) of the desired 1-(chroman-6-yl)-4-(4-methylbenzyl)piperazine as a white solid, TLC $R_f$ 0.35 (30% ethyl acetate-hexane). A solution of this material in 1 mL of ethanol is treated with oxalic acid (11 mg) and concentrated to give 1-(chroman-6-yl)-4-(4-methylbenzyl) piperazine oxalate (Compound 4) 51 mg, m.p. 199° C.

EXAMPLE 5

The following compounds are prepared essentially according to the procedures set forth above in Examples 3 and 4.

(a) 1-(1,4-benzodioxan-6-yl)-4-(4-chlorobenzyl) piperazine oxalate (Compound 3, m.p. 213–215° C.)

(b) 1-(1,4-benzodioxan-6-yl)-4-(4-methylbenzyl) piperazine oxalate (Compound 5, m.p. 200–201° C.)

(c) 1-(1,4-benzodioxan-6-yl)-4-(4-methoxybenzyl) piperazine oxalate (Compound 6, m.p. 193–195° C.)

(d) 1-(1,4-benzodioxan-6-yl)-4-(3-chlorobenzyl) piperazine oxalate (Compound 7, m.p. 213–215C.)

(e) 1-(1,4-benzodioxan-6-yl)-4-(3-methoxybenzyl) piperazine oxalate (Compound 2, m.p. 213–215° C.)

(f) 1-(1,4-benzodioxan-6-yl)-4-(2-chlorobenzyl) piperazine oxalate (Compound 8, m.p. 175° C.)

(g) 1-(1,4-benzodioxan-6-yl)-4-(2-methoxybenzyl) piperazine oxalate (Compound 9, m.p. 143° C.)

(h) 1-(1,4-benzodioxan-6-yl)-4-benzylpiperazine hydrochloride (Compound 10, m.p. 143–145° C.)

(i) 1-(chroman-6-yl)-4-(4-chlorobenzyl)piperazine oxalate (Compound 11).

EXAMPLE 6

Assays For $D_2$, $D_3$ and $D_4$ Receptor Binding Activity

The pharmaceutical utility of compounds of this invention is indicated by the assays for dopamine receptor subtype affinity described below.

Pellets of COS cells containing recombinantly produced $D_2$, $D_3$ or $D_4$ receptors from human are used for the assays. The sample is homogenized in 100 volumes (w/vol) of 0.05 M Tris HCl buffer at 40° C. and pH 7.4. The sample is then centrifuged at 30,000×g and resuspended and rehomogenized. The sample is then centrifuged as described and the final tissue sample is frozen until use. The tissue is resuspended 1:20 (wt/vol) in 0.05 M Tris HCl buffer containing 100 mM NaCl.

Incubations are carried out at 48° C. and contain 0.4 ml of tissue sample, 0.5 nM ³H-YM 09151-2 and the compound of interest in a total incubation of 1.0 ml. Nonspecific binding is defined as that binding found in the presence of 1 mM spiperone; without further additions, nonspecific binding is less than 20% of total binding. Binding characteristics for representative compounds of the invention for the $D_2$, $D_3$ and $D_4$ receptor subtypes are shown in Table 2 for rat striatal homogenates.

TABLE 2

| Compound Number[1] | $D_4$ $K_i$ (nM) | $D_3$ $K_i$ (nM) | $D_2$ $K_i$ (nM) |
|---|---|---|---|
| 1 | 11 | 3662 | >4000 |
| 2 | 37 | 2569 | 2587 |
| 3 | 25 | 2625 | >4000 |
| 4 | 35 | 2992 | 2309 |

[1]Compound numbers relate to compounds shown in FIG. 1.

The above data are representative of the $K_i$ values for compounds of the invention; all compounds of the invention are active in the above assay. The binding constants of compounds of Formula I for the $D_4$ receptor, expressed in nM, generally range from about 0.5 nanomolar (nM) to about 100 nanomolar (nM). These compounds typically have binding constants for the $D_2$ receptor of at least about 1000 nM. Thus, the compounds of the invention are generally at least about 10 time more selective for the $D_4$ receptor than the $D_2$ receptor. Preferably, these compounds are at least 20, and more preferably at least 25–50, times more selective for the $D_4$ receptor than the $D_2$ receptor. Most preferably, these compounds are at least about 100 times more selective for the $D_4$ receptor than the $D_2$ receptor. Similarly, the compounds of the invention are generally at least about 10 time more selective for the $D_4$ receptor than the $D_3$ receptor.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A pharmaceutical composition comprising a pharmaceutically acceptable carrier and a compound of the formula:

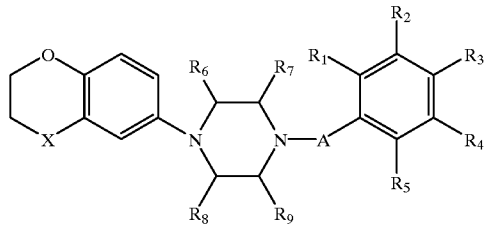

or the pharmaceutical acceptable acid addition salts thereof wherein:

A is methylene;

$R_1$, $R_2$, $R_3$, $R_4$ and $R_5$ are the same or different and represent hydrogen, halogen, $C_1$–$C_6$ alkyl, $C_1$–$C_6$ alkoxy, $C_1$–$C_4$ alkylthio, hydroxy, amino, mono- or di($C_1$–$C_6$)alkylamino, cyano, nitro, trifluoromethyl or trifluoromethoxy provided that at least one of $R_1$–$R_5$ is other than hydrogen;

$R_6$, $R_7$, $R_8$ and $R_9$ are the same or different and are hydrogen or $C_1$–$C_6$ alkyl; and X is oxygen, a bond, or $C_1$–$C_2$ alkylene.

2. A pharmaceutical composition according to claim 1, wherein $R_1$, $R_2$, $R_3$, $R_4$, and $R_5$ independently represent hydrogen, halogen, $C_1$–$C_6$ alkyl, or $C_1$–$C_6$ alkoxy provided that at least one of $R_1$–$R_5$ is other than hydrogen.

3. A pharmaceutical composition according to claim 1, wherein $R_1$, $R_2$, and $R_5$ are hydrogen.

4. A pharmaceutical composition according to claim 1, wherein $R_1$, $R_2$, and $R_5$ are hydrogen and $R_3$ and $R_4$ independently represent hydrogen, halogen, $C_1$–$C_6$ alkyl, or $C_1$–$C_4$ alkoxy, where not both $R_3$ and $R_4$ are hydrogen.

5. A pharmaceutical composition according to claim 1, wherein $R_3$ and $R_4$ independently represent hydrogen, fluoro, chloro, bromo, methyl, ethyl, methoxy, or ethoxy, where not both $R_3$ and $R_4$ are hydrogen.

6. A pharmaceutical composition according to claim 1, wherein X is oxygen.

7. A pharmaceutical composition according to claim 1, wherein $R_1$, $R_2$, $R_3$, $R_4$, and $R_5$ independently represent hydrogen, halogen, $C_1$–$C_6$ alkyl, or $C_1$–$C_6$ alkoxy provided that at least one of $R_1$–$R_5$ is other than hydrogen.

8. A pharmaceutical composition according to claim 1, wherein $R_1$, $R_2$, and $R_5$ are hydrogen.

9. A pharmaceutical composition according to claim 1, wherein $R_1$, $R_2$, and $R_5$ are hydrogen and $R_3$ and $R_4$ independently represent hydrogen, halogen, $C_1$–$C_6$ alkyl, or $C_1$–$C_4$ alkoxy, where not both $R_3$ and $R_4$ are hydrogen.

10. A pharmaceutical composition according to claim 1, wherein $R_3$ and $R_4$ independently represent hydrogen, fluoro, chloro, bromo, methyl, ethyl, methoxy, or ethoxy, where not both $R_3$ and $R_4$ are hydrogen.

11. A pharmaceutical composition comprising a pharmaceutically acceptable carrier and a compound of the formula:

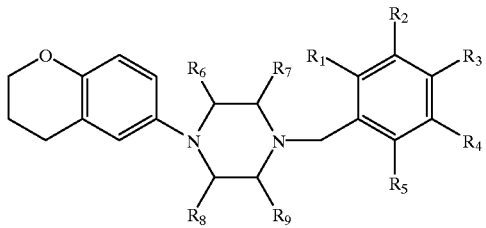

or the pharmaceutically acceptable acid addition salts thereof wherein:

$R_1$, $R_2$, $R_3$, $R_4$ and $R_5$ are the same or different and represent hydrogen, halogen, $C_1$–$C_6$ alkyl, $C_1$–$C_6$ alkoxy, $C_1$–$C_4$ alkylthio, hydroxy, amino, mono- or di($C_1$–$C_6$)alkylamino, cyano, nitro, trifluoromethyl or trifluoromethoxy; and $R_6$, $R_7$, $R_8$ and $R_9$ are the same or different and are hydrogen or $C_1$–$C_5$ alkyl.

12. A pharmaceutical composition according to claim 1, wherein $R_1$, $R_2$, $R_3$, $R_4$, and $R_5$ independently represent hydrogen, halogen, $C_1$–$C_6$ alkyl, or $C_1$–$C_6$ alkoxy.

13. A pharmaceutical composition according to claim 11, wherein $R_1$, $R_2$, and $R_5$ are hydrogen.

14. A pharmaceutical composition according to claim 16, wherein $R_1$, $R_2$, and $R_5$ are hydrogen and $R_3$ and $R_4$ independently represent hydrogen, halogen, $C_1$–$C_6$ alkyl, or $C_1$–$C_4$ alkoxy, where not both $R_3$ and $R_4$ are hydrogen.

15. A pharmaceutical composition according to claim 11, wherein $R_3$ and $R_4$ independently represent hydrogen, fluoro, chloro, bromo, methyl, ethyl, methoxy, or ethoxy, where not both $R_3$ and $R_4$ are hydrogen.

16. A pharmaceutical composition comprising a pharmaceutically acceptable carrier and a compound of the formula:

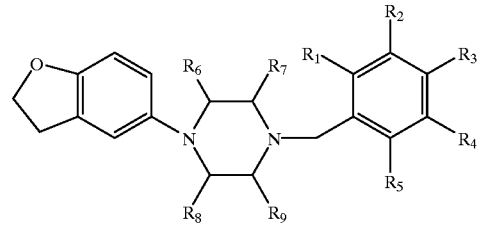

or the pharmaceutically acceptable acid addition salts thereof wherein:

$R_1$, $R_2$, $R_3$, $R_4$ and $R_5$ are the same or different and represent hydrogen, halogen, $C_1$–$C_6$ alkyl, $C_1$–$C_6$ alkoxy, $C_1$–$C_4$ alkylthio, hydroxy, amino, mono- or di($C_1$–$C_6$)alkylamino, cyano, nitro, trifluoromethyl or trifluoromethoxy; and $R_6$, $R_7$, $R_8$ and $R_9$ are the same or different and are hydrogen or $C_1$–$C_6$ alkyl.

17. A pharmaceutical composition comprising a pharmaceutically acceptable carrier and a compound of the formula:

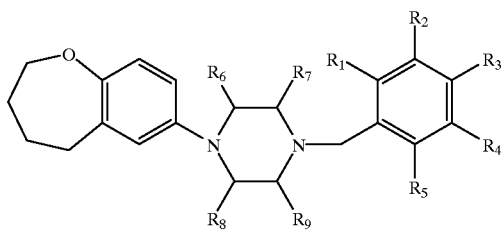

our the pharmaceutically acceptable acid addition salts thereof wherein: $R_1$, $R_2$, $R_3$, $R_4$ and $R_5$ are the same or different and represent hydrogen, halogen, $C_1$–$C_6$ alkyl, $C_1$–$C_6$ alkoxy, $C_1$–$C_4$ alkylthio, hydroxy, amino, mono- or di($C_1$–$C_6$)alkylamino, cyano, nitro, trifluoromethyl or trifluoromethoxy; and $R_6$, $R_7$, $R_8$ and $R_9$ are the same or different and are hydrogen or $C_1$–$C_6$ alkyl.

18. A pharmaceutical composition according to claim 16, wherein;

$R_1$, $R_2$, and $R_5$ are hydrogen; and $R_3$ and $R_4$ independently represent hydrogen, halogen, $C_1$–$C_6$ alkyl, or $C_1$–$C_4$ alkoxy, where not both $R_3$ and $R_4$ are hydrogen.

19. A pharmaceutical composition according to claim 17;

$R_1$, $R_2$, and $R_5$ are hydrogen; and $R_3$ and $R_4$ independently represent hydrogen, halogen, $C_1$–$C_6$ alkyl, or $C_1$–$C_4$ alkoxy, where not both $R_3$ and $R_4$ are hydrogen.

20. A pharmaceutical composition according to claim 1, wherein the compound or salt is 1-(1,4-benzodioxan-6-yl)-4-(4-fluorobenzyl)piperazine.

21. A pharmaceutical composition according to claim 1, wherein the compound or salt is 1-(1,4-benzodioxan-6-yl)-4-(4-chlorobenzyl)piperazine.

22. A pharmaceutical composition according to claim 1, wherein the compound or salt is 1-(1,4-benzodioxan-6-yl)-4-(4-methylbenzyl)piperazine.

23. A pharmaceutical composition according to claim 1, wherein the compound or salt is 1-(1,4-benzodioxan-6-yl)-4-(4-methoxybenzyl)piperazine.

24. A pharmaceutical composition according to claim 1, wherein the compound or salt is 1-(1,4-benzodioxan-6-yl)-4-(3-chlorobenzyl)piperazine.

25. A pharmaceutical composition according to claim 1, wherein the compound or salt is 1-(1,4-benzodioxan-6-yl)-4-(3-methoxybenzyl)piperazine.

26. A pharmaceutical composition according to claim 1, wherein the compound or salt is 1-(1,4-benzodioxan-6-yl)-4-(2-chlorobenzyl)piperazine.

27. A pharmaceutical composition according to claim 1, wherein the compound or salt is 1-(1,4-benzodioxan-6-yl)-4-(2-methoxybenzyl)piperazine.

28. A pharmaceutical composition according to claim 1, wherein the compound or salt is 1-(chroman-6-yl)-4-(4-methylbenzyl)piperazine.

29. A pharmaceutical composition according to claim 1, wherein the compound or salt is 1-(chroman-6-yl)-4-(4-chlorobenzyl)piperazine.

* * * * *